(12) United States Patent
Reddy et al.

(10) Patent No.: US 7,518,019 B2
(45) Date of Patent: Apr. 14, 2009

(54) PROCESSES FOR PREPARING SERTRALINE HYDROCHLORIDE CRYSTALLINE FORMS

(75) Inventors: Bandi Parthasaradhi Reddy, Hyderabad (IN); Kura Rathnakar Reddy, Hyderabad (IN); Rapolu Raju Reddy, Hyderabad (IN); Dasari Muralidhara Reddy, Hyderabad (IN); Kesireddy Subash Chander Reddy, Hyderabad (IN)

(73) Assignee: Hetero Drugs Limited, Hyderabad (IN)

( * ) Notice: Subject to any disclaimer, the term of this patent is extended or adjusted under 35 U.S.C. 154(b) by 78 days.

(21) Appl. No.: 11/444,683

(22) Filed: Jun. 1, 2006

(65) Prior Publication Data

US 2007/0282129 A1    Dec. 6, 2007

(51) Int. Cl.
*C07C 209/00*    (2006.01)
*C07C 211/00*    (2006.01)

(52) U.S. Cl. ........................ 564/437; 564/308
(58) Field of Classification Search .................. None
See application file for complete search history.

(56) References Cited

U.S. PATENT DOCUMENTS

| | | | |
|---|---|---|---|
| 4,536,518 A | 8/1985 | Welch, Jr. et al. | |
| 5,248,699 A | 9/1993 | Sysko et al. | |
| 5,734,083 A | 3/1998 | Wilson et al. | |
| 6,495,721 B1 | 12/2002 | Schwartz et al. | |
| 2001/0041815 A1 | 11/2001 | Aronhime et al. | |
| 2004/0030190 A1 | 2/2004 | Borochovitch et al. | |
| 2004/0102523 A1 | 5/2004 | Broquaire et al. | |
| 2005/0032906 A1 | 2/2005 | Bonifacio et al. | |

FOREIGN PATENT DOCUMENTS

| | | |
|---|---|---|
| CA | 2448279 A1 | 5/2002 |
| WO | 0132601 A1 | 5/2001 |
| WO | 2004041773 A1 | 5/2004 |

OTHER PUBLICATIONS

Examiner's Report dated Sep. 17, 2007.
Banga S, Chawla G, Bansal AK. New trends in crystallization of active pharmaceutical ingredients. Business Briefing: Pharmagenerics 2004, 1-5 (Nov).

*Primary Examiner*—Karl J Puttlitz
(74) *Attorney, Agent, or Firm*—Caesar, Rivise, Bernstein, Cohen & Pokotilow, Ltd.

(57) ABSTRACT

The present invention discloses novel and improved processes for preparation of sertraline hydrochloride crystalline form II. Thus, for example, sertraline free base is dissolved in isoamyl alcohol at 25-30° C., pH of the mass is adjusted to 2.0 with conc. hydrochloric acid (36%) at 25-30° C. and then stirred for 14 hours at 25-30° C. Filtered the solid and dried at 65° C. for 4 hours to give sertraline hydrochloride crystalline form II. The present invention also provides a novel process for preparation of sertraline hydrochloride crystalline form I.

13 Claims, 2 Drawing Sheets

PROCESSES FOR PREPARING SERTRALINE HYDROCHLORIDE CRYSTALLINE FORMS

FIELD OF THE INVENTION

The present invention relates to improved processes for preparation of sertraline hydrochloride crystalline form II. The present invention also provides a novel process for preparation of sertraline hydrochloride crystalline form I.

BACKGROUND OF THE INVENTION

U.S. Pat. No. 4,536,518, which is herein incorporated by reference, disclosed cis-isomeric derivatives of 4-phenyl-1,2,3,4-tetrahydro-1-naphthalenamine and their pharmaceutically acceptable salts. These compounds act to block the synaptosomal uptake of serotonin (5-hydroxytryptamine), thereby alleviating serotonin abnormalities at central receptor sites. Among them sertraline hydrochloride, chemically (1S,4S)-4-(3,4-dichlorophenyl)-1,2,3,4-tetrahydro-N-methyl-1-naphthalenamine hydrochloride is a selective serotonin reuptake inhibitor (SSRI). Sertraline hydrochloride is represented by the following structure:

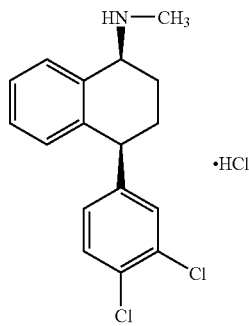

Sertraline hydrochloride can exist in different crystalline forms, which differ from each other in terms of stability, physical properties, spectral data and methods of preparation.

Processes for the preparations of sertraline, its pharmaceutically acceptable salts and related compounds were described in U.S. Pat. No. 4,536,518 (Pfizer Inc.). U.S. Pat. No. 4,536,518 described a process for preparation of sertraline hydrochloride by treating an ethyl acetate/ether solution of sertraline free base with gaseous hydrogen chloride.

U.S. Pat. No. 5,248,699 (Pfizer Inc.) described five crystalline forms of sertraline hydrochloride (Forms I, II, III, IV and V), and characterizes them by single crystal x-ray analysis, powder x-ray diffraction, infra-red spectroscopy, and differential scanning calorimetry. U.S. Pat. No. 5,248,699 further described that the synthetic procedure described and exemplified in U.S. Pat. No. 4,536,518 produces the sertraline hydrochloride crystalline form designated herein as Form II. The patent also reported that form II is produced by rapid crystallization of sertraline hydrochloride from an organic solvent, including isopropyl alcohol, hexane, generally describes methods for making sertraline hydrochloride forms I to V. According to this patent, the preferential formation of Forms I, II or IV in an acidic solution consisting of isopropyl alcohol, hexane, acetone, methyl isobutyl ketone, glacial acetic acid and ethyl acetate depends on the rapidity of crystallization.

U.S. Pat. No. 5,734,083 (Torcan Chemical Ltd.) discloses a polymorphic form of sertraline hydrochloride (T1), together with the process of preparation.

U.S. Pat. No. 6,495,721 (Teva Pharm. Ind.) describes various polymorphic forms of sertraline hydrochloride such as, crystalline forms (forms VI, VII, VIII, IX and X), amorphous form and solvated forms (ethanolate and methanolate), and processes for their preparation thereof. The patent also describes a process for preparing sertraline hydrochloride form V by crystallization from various solvents rather than by sublimation.

U.S. Pat. No. 6,495,721 further discloses processes for preparing sertraline hydrochloride form II comprising the steps of dissolving sertraline free base or its mandelate salt in an organic solvent, selected from the group consisting of ethyl acetate, acetone, hexane, t-butyl methyl ether, isopropyl alcohol, n-butanol, t-butanol, isobutanol, and cyclohexane, to form a solution; adding hydrogen chloride to the solution; heating the solution for a time sufficient to induce the formation of sertraline hydrochloride; and isolating sertraline hydrochloride form II.

U.S. Patent Application No. 2001/0041815 A1 (Teva Pharm. Ind.) discloses various polymorphic forms (XI, XII, XIII, XIV, XV and XVI) of sertraline hydrochloride and processes for their preparation.

PCT Patent Publication No. WO 01/32601 A1 (Ciba Specialty Chem.) discloses polymorphic forms of sertraline hydrochloride such as crystalline form (CSC2), crystalline forms of alcohol solvates (ethanol solvate, isopropanol solvate and methanol solvate) and crystalline forms of hydrates (CSC1) and processes for their preparation. The publication also describes, a process for the preparation of the amorphous form of sertraline hydrochloride, and different processes for the preparation of sertraline hydrochloride polymorphic forms I, II, V, and T1.

PCT Patent Publication No. WO 01/32601 A1 further describes a process for the preparation of polymorphic form II of sertraline hydrochloride, wherein a solution of sertraline free amine is seeded with some crystals of polymorphic form II before addition of a solution of hydrogen chloride, or wherein a stirred suspension of sertraline hydrochloride polymorphic form V is stirred with some seeding crystals of sertraline hydrochloride polymorphic form II, or wherein sertraline hydrochloride alcohol solvate is dried at temperatures from 0-30° C. in a high vacuum of less than 1 mbar, or wherein suspensions of sertraline hydrochloride polymorphic forms CSC1, CSC2 or T1 are stirred with some seeding crystals of sertraline hydrochloride polymorphic form II.

U.S. Patent Application No. 2004/0030190 A1 (Teva Pharm. Ind.) describes a reproducible process for preparation of sertraline hydrochloride form II substantially free of crystalline sertraline hydrochloride form I, which comprises, providing a solution of sertraline base, or a solution or slurry of sertraline mandelate, in an organic solvent selected from the group consisting of n-butanol, cyclohexane, ethyl acetate, acetone, hexane, t-butyl methyl ether and dimethylformamide; contacting the solution or the slurry with a flow of gaseous hydrogen chloride at a suitable rate at a temperature within the range of from about 30° C. to about 60° C., during which time sertraline hydrochloride form II forms, wherein the temperature is kept substantially constant during the gas flow; and filtering the sertraline hydrochloride form II at a temperature of from about 30° C. to about 60° C. to obtain sertraline hydrochloride form II substantially free of sertraline hydrochloride form I.

PCT Patent Publication No. WO 2004/041773 A1 (Torrent Research Centre) describes a process for the preparation of sertraline hydrochloride form V by dissolving or suspending sertraline mandelate in a solvent selected from the group comprising of methanol, ethanol, n-propyl alcohol, isopropyl alcohol, n-butyl alcohol, t-butyl alcohol, isobutyl alcohol, water or mixtures thereof, reducing the pH of the solution or the suspension with HCl and isolating sertraline hydrochloride form V.

U.S. Patent Application No. 2005/0032906 A1 describes a method of selectively preparing pure sertraline hydrochloride form II, comprising the step of crystallizing sertraline hydrochloride in an acidic solution of an organic solvent selected from the group consisting of n-propanol, n-pentanol, n-hexanol, n-heptanol, n-ocatnol, acetonitrile, 1-methyl-2-piperidone, and mixtures thereof.

According to one object of the present invention is to provide novel and improved processes for preparing highly pure sertraline hydrochloride crystalline form II.

It has been found that the sertraline hydrochloride form II is obtained consistently contrary to the prior art process. The prior art processes require careful control on the temperature during the addition of hydrochloric acid and isolation of sertraline hydrochloride form II. One advantage of the novel process is that no such control is necessary according to the novel process and therefore, the process of the invention is commercially viable.

According to another object of the present invention is to provide a novel process for preparing sertraline hydrochloride crystalline form I.

DETAILED DESCRIPTION OF THE INVENTION

According to one aspect of the present invention, there is provided a process for preparing sertraline hydrochloride crystalline form II which comprises:
a) adding sertraline free base or sertraline mandelate to a solvent selected from isoamyl alcohol, tert-amyl alcohol and an ester formed by isoamyl alcohol and $C_1$-$C_3$-carboxylic acid;
b) adding hydrochloric acid; and
c) isolating sertraline hydrochloride crystalline form II.

Preferably, sertraline free base is dissolved in the solvent before the addition of hydrochloric acid. Preferable solvents to which sertraline free base or sertraline mandelate may be added are isoamyl alcohol, tert-amyl alcohol, isoamyl formate and isoamyl acetate. More preferable solvents to which sertraline free base or sertraline mandelate may be added are isoamyl alcohol and tert-amyl alcohol, and most preferable being isoamyl alcohol.

If sertraline mandelate is used as starting material the sertraline mandelate may be dissolved or suspended in the organic solvent before the addition of hydrochloric acid.

Hydrochloric acid may then be added in any form that is as an aqueous hydrochloric acid, hydrogen chloride gas or hydrogen chloride in an organic solvent such as methanol, ethanol, isopropyl alcohol, isoamyl alcohol, acetone and ethyl acetate. Sertraline hydrochloride obtained may be isolated immediately or after stirring for a sufficient time to maximize the yield of the sertraline hydrochloride form II.

Isolation of sertraline hydrochloride crystalline form II may be initiated by a method usually known in the art such as cooling, seeding, partial removal of the solvent from the solution, addition of precipitating solvent or a combination thereof.

Preferably, isolation may be carried out by cooling to obtain sertraline hydrochloride crystalline form II.

The temperature of the reaction medium is not critical as long as sertraline hydrochloride can be isolated as solid from the reaction medium. Preferably the addition of hydrochloride to the solution of sertraline free base and isolation of sertraline hydrochloride crystalline form II are carried out at about 0° C. to boiling temperature of the solvent used. More preferably, the addition of hydrochloric acid is carried out at about 0° C. to 60° C., still more preferably at about 0° C. to 40° C. and most preferably at about 0° C. to 30° C.

It has also been found that the sertraline hydrochloride form II is obtained consistently contrary to the prior art process. The prior art processes require careful control on the temperature during the addition of hydrochloric acid and isolation of sertraline hydrochloride form II. One advantage of the novel process is that no such control is necessary according to the novel process. Thus, for example, it has been found that when n-amyl alcohol is used as solvent instead of isoamyl alcohol, the sertraline hydrochloride is obtained in crystalline form I if the addition of hydrochloric acid is carried out at 25° C. or below and sertraline hydrochloride crystalline form II is obtained if the addition of hydrochloric acid is carried out above 25° C.

According to another aspect of the present invention, there is provided a process for preparing sertraline hydrochloride crystalline form II which comprises:
a) stirring sertraline hydrochloride in a solvent selected from isoamyl alcohol, tert-amyl alcohol and an ester formed by isoamyl alcohol and $C_1$-$C_3$-carboxylic acid for a time sufficient for conversion to sertraline hydrochloride crystalline form II; and
b) isolating sertraline hydrochloride crystalline form II.

Temperature at which sertraline hydrochloride may be stirred in the solvent is not critical for obtaining sertraline hydrochloride form II.

Preferably, the stirring in step (a) may be carried out at about 0° C. to boiling temperature of the solvent used. More preferably, the stirring is carried out at about 0° C. to 60° C., still more preferably at about 0° C. to 40° C. and most preferably at about 0° C. to 30° C.

Preferable solvent used in step (a) is selected from the group consisting of isoamyl alcohol, tert-amyl alcohol, isoamyl formate and isoamyl acetate, more preferable solvent is selected from isoamyl alcohol and tert-amyl alcohol, and most preferable solvent being isoamyl alcohol.

Preferably sertraline hydrochloride used as the starting material is added to the solvent to form a slurry and the slurry is stirred for a time sufficient to conversion to sertraline hydrochloride form II and then the sertraline hydrochloride form II is isolated.

The sertraline hydrochloride used in the process of the invention may be in any polymorph, hydrate or solvate other than sertraline hydrochloride form II.

Various polymorphs of sertraline hydrochloride are described in U.S. Pat. Nos. 5,248,699, 5,734,083 and U.S. Patent Application No. 2001/0041815 A1, and these forms may be used as starting materials.

Isolation of sertraline hydrochloride crystalline form II may be initiated by a method usually known in the art such as cooling, seeding, partial removal of the solvent from the solution, addition of precipitating solvent or a combination thereof.

Preferably, isolation may be carried out by cooling or by using a precipitating solvent to obtain sertraline hydrochloride crystalline form II.

It has also been found that the sertraline hydrochloride form II is obtained consistently contrary to the prior art process. The prior art processes require careful control on the temperature during stirring of sertraline hydrochloride in a solvent and isolation of sertraline hydrochloride form II. One advantage of the novel process is that no such control is necessary according to the novel process. Thus, for example, it has been found that when n-amyl alcohol is used as solvent instead of isoamyl alcohol and when addition of hydrochloric acid is carried out at 25° C. or below, the sertraline hydrochloride is obtained in crystalline form I and not the crystalline form II.

According to another aspect of the present invention, there is provided a process for preparing sertraline hydrochloride crystalline form I which comprises:
a) adding sertraline free base or sertraline mandelate to n-amyl alcohol;
b) adding hydrochloric acid at 25° C. or below; and
c) isolating sertraline hydrochloride crystalline form I.

Preferably, sertraline free base is dissolved in n-amyl alcohol before the addition of hydrochloric acid. If sertraline mandelate is used as starting material the sertraline mandelate may be dissolved or suspended in n-amyl alcohol before the addition of hydrochloric acid.

Hydrochloric acid may then be added in any form that is as an aqueous hydrochloric acid, hydrogen chloride gas or hydrogen chloride in an organic solvent such as methanol, ethanol, isopropyl alcohol, isoamyl alcohol, acetone and ethyl acetate. Sertraline hydrochloride obtained may be isolated immediately or after stirring for a sufficient time to maximize the yield of the sertraline hydrochloride form I.

Isolation of sertraline hydrochloride crystalline form I may be initiated by a method usually known in the art such as cooling, seeding, partial removal of the solvent from the solution, addition of precipitating solvent or a combination thereof.

Preferably, isolation may be carried out by cooling to obtain sertraline hydrochloride crystalline form I. Preferably the addition of hydrochloride to the solution of sertraline free base and isolation of sertraline hydrochloride crystalline form I are carried out at below about 20° C. More preferably, the addition of hydrochloric acid is carried out between about 0° C. to 20° C.

The sertraline free base or sertraline mandelate used as starting material in the above processes may be obtained by known methods such as those described in U.S. Pat. No. 4,536,518 and PCT Patent Application No. PCT/IN05/00197.

Figure 1:
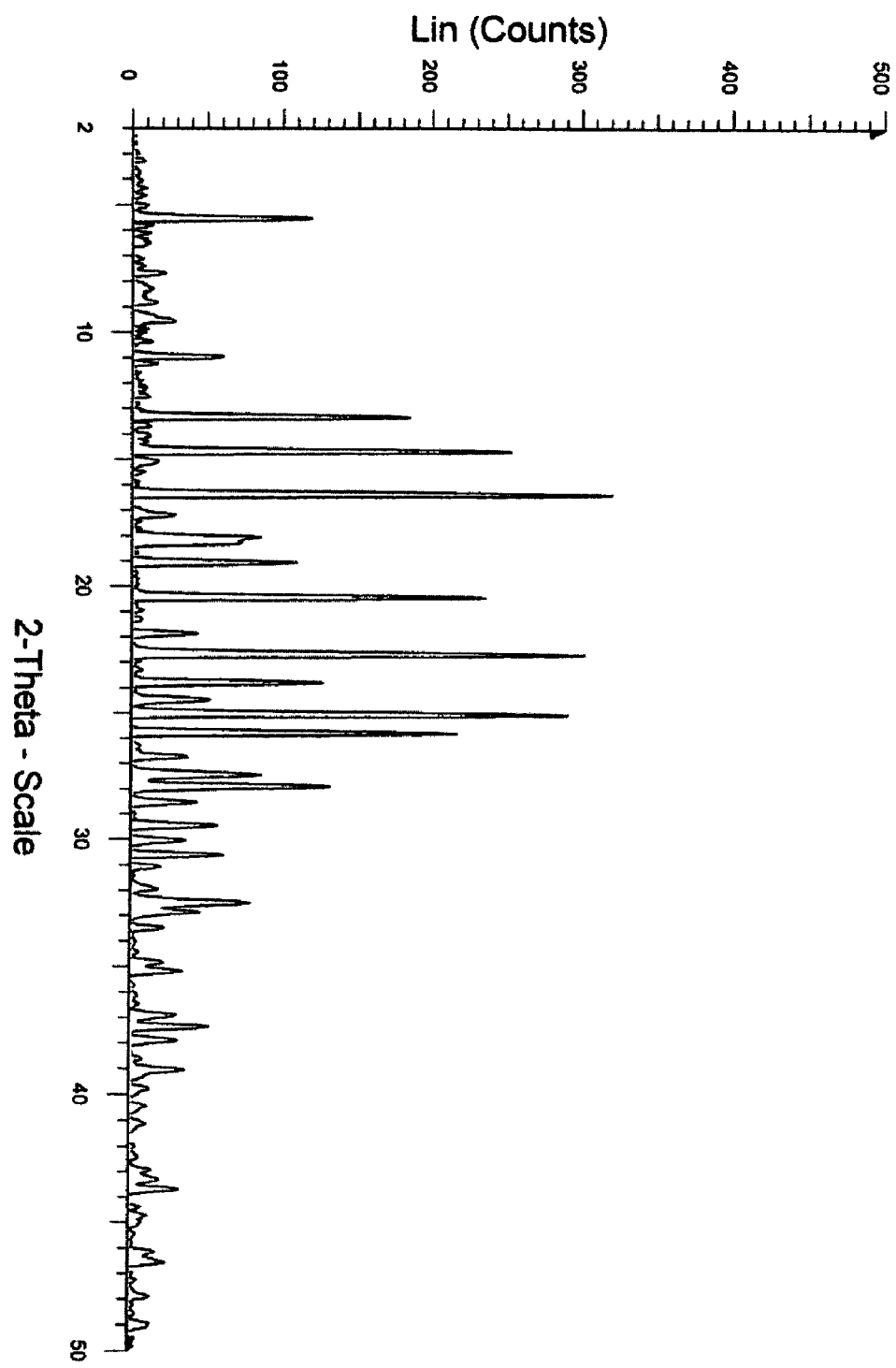
FIG. 1 is an X-ray powder diffraction spectrum of sertraline hydrochloride crystalline form II.
Figure 2:
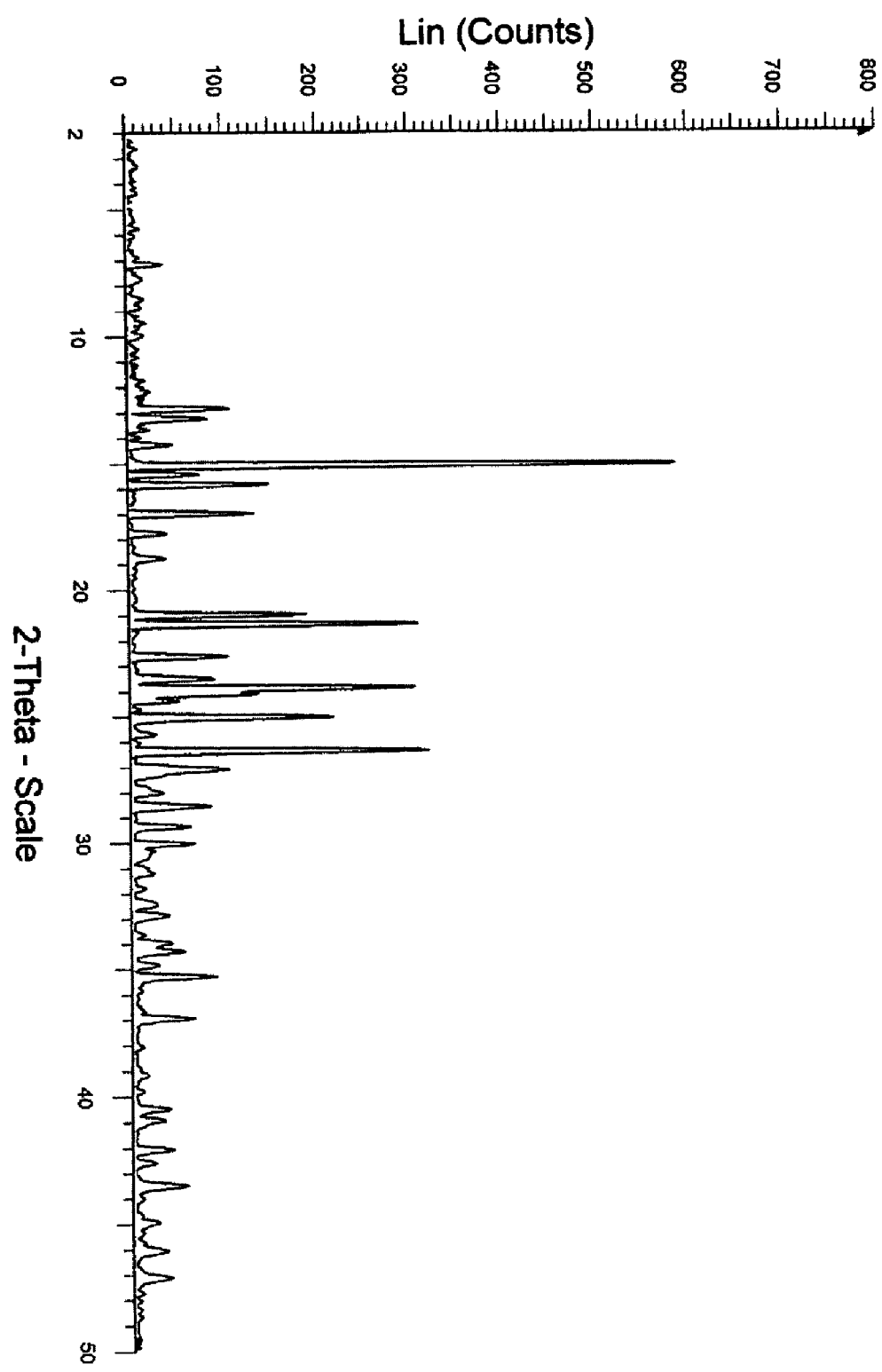
FIG. 2 is an X-ray powder diffraction spectrum of sertraline hydrochloride crystalline form I.

X-Ray powder diffraction spectrum was measured on a Bruker axs D8 advance X-ray powder diffractometer having a Copper-Kα radiation. Approximately 1 gm of sample was gently flattened on a sample holder and scanned from 2 to 50 degrees two-theta, at 0.03 degrees two-theta per step and a step time of 0.5 seconds. The sample was simply placed on the sample holder. The sample was rotated at 30 rpm at a voltage 40 KV and current 35 mA.

The following examples are given for the purpose of illustrating the present invention and should not be considered as limitations on the scope or spirit of the invention.

PREPARATIVE EXAMPLE 1a

The mixture of 4-(3,4-Dichlorophenyl)-3,4-dihydro-N-methyl-1(2H)-naphthalenimine (10 gm), 5% Pd/CaCO$_3$ (grade-21, 0.6 gm), water (2 ml) and methanol (150 ml) is taken in a hydrogenation flask and then subjected to hydrogenation under a hydrogen pressure of 0.5 Kg at 20-35° C. for 3 hours 30 minutes. The catalyst is removed by filtration and the solvent is evaporated completely under vacuum to obtain cis-(±)-4-(3,4-dichlorophenyl)-1,2,3,4-tetrahydro-N-methyl-naphthalenamine. (cis-(±):trans-(±): 99.8:0.2).

To the above reaction mass ethyl acetate (65 ml) and water (20 ml) are added and the pH is adjusted to 9.5-11.0 with aqueous sodium hydroxide (50%). The organic layer is washed with 10% sodium chloride solution (20 ml) and then subjected to carbon treatment. Then the reaction mass is heated to 45-50° C., D-(−)-mandelic acid (2.9 gm) is added at 45-50° C. and stirred for 2 hours at the same temperature. The mass is cooled to 25-35° C., stirred for 12 hours at 25-35° C., then cooled to 0-5° C. and stirred for 1 hour at the same temperature. Filtered the mass and washed with ethyl acetate, methanol (15 ml) is added and then heated to reflux. The contents are stirred for 1 hour at reflux and cooled to 25-35° C. Then the reaction mass is cooled to 0-5° C. and stirred for 1 hour at 0-5° C. Filtered the solid, washed with methanol and dried to give 4.6 gm of (1S-cis)-4-(3,4-dichlorophenyl)-1,2,3,4-tetrahydro-N-methyl-naphthalenamine mandelate (trans-(±): not detected).

PREPARATIVE EXAMPLE 1b

Water (30 ml) and ethyl acetate (35 ml) are added to (1S-cis)-4-(3,4-dichlorophenyl)-1,2,3,4-tetrahydro-N-methyl-naphthalenamine mandelate (obtained in step-Ia), cooled to 10-18° C. and aqueous sodium hydroxide (50%) is slowly added for 1 hour 30 minutes at 10-18° C. (to adjust the pH to 9.5-11.0). The contents are stirred for 30-45 minutes, separated the aqueous layer and discarded it. Activated carbon (0.25 gm) is added to the reaction mass, stirred for 15-30 minutes, filtered and washed with ethyl acetate (5 ml). Distilled off ethyl acetate under reduced pressure until the mass temperature reaches to 50-55° C. to give 3.1 gm of sertraline free base as residue (HPLC purity: 99.7%).

EXAMPLE 1

Sertraline free base (residue, 5 gm) is dissolved in isoamyl alcohol (35 ml) at 25-30° C., pH of the mass is adjusted to 2.0 with conc. hydrochloric acid (36%) at 25-30° C. and then stirred for 14 hours at 25-30° C. Filtered the solid and dried at 65° C. for 4 hours to give 2.4 gm of sertraline hydrochloride crystalline form II.

EXAMPLE 2

Sertraline free base (10 gm) is dissolved in isoamyl alcohol (70 ml) at 25-30° C., pH of the mass is adjusted to 2.0 by passing hydrogen chloride gas at 2-4° C., raised the mass temperature to 30° C. during 2 hours and then stirred for 4 hours at 25-30° C. Filtered the solid and dried for 7 hours at 60° C. to give 7.2 gm of sertraline hydrochloride crystalline form II.

EXAMPLE 3

Sertraline free base (10 gm) is dissolved in isoamyl alcohol (70 ml) at 25-30° C., pH of the mass is adjusted to 2.0 with conc. hydrochloric acid (36%) at 10-15° C., raised the mass temperature to 25° C. during 30 minutes and then stirred for 3 hours 30 minutes at 25-30° C. Filtered the solid and dried for 7 hours at 60° C. to give 5.4 gm of sertraline hydrochloride crystalline form II.

EXAMPLE 4

Sertraline free base (5 gm) is dissolved in isoamyl alcohol (35 ml) at 25-30° C., heated to 40-45° C., pH of the mass is adjusted to 2.0 with conc. hydrochloric acid (36%) at 40-45° C. and then stirred for 3 hours 30 minutes at 45-48° C. Filtered the solid and dried for 15 hours at 60° C. to give 2.5 gm of sertraline hydrochloride crystalline form II.

EXAMPLE 5

Isoamyl alcohol (30 ml) and ethyl acetate (30 ml) are added to sertraline free base (10 gm) under stirring at 25-30° C., pH of the mass is adjusted to 2.0 with conc. hydrochloric acid (36%) at 25-30° C. and then stirred for 4 hours 15 minutes at 25-30° C. Filtered the solid and dried for 7 hours at 60° C. to give 7.4 gm of sertraline hydrochloride crystalline form II.

EXAMPLE 6

Sertraline free base (10 gm) is dissolved in isoamyl alcohol (70 ml) at 25-30° C., cooled to 15° C. and then pH of the mass is adjusted to 2.0 with conc. hydrochloric acid (36%) at 10-15° C. The mass temperature is raised to 25° C., stirred for 2 hours at 25-30° C. and then filtered the solid. Diisopropyl ether is added to the resulting wet solid at 25-30° C. and stirred for 20 minutes at 25-30° C. Filtered the solid and dried for 2 hours at 60° C. to give 7.3 gm of sertraline hydrochloride crystalline form II.

EXAMPLE 7

Sertraline free base (10 gm) is dissolved in n-amyl alcohol (70 ml) at 30-35° C., cooled to 11° C. and then pH of the mass is adjusted to 2.0 with conc. hydrochloric acid (36%) at 10-12° C. The reaction mass is stirred for 8 hours at 10-15° C. Filtered the solid and dried at 60° C. for 15 hours to give 6.2 gm of sertraline hydrochloride crystalline form I.

EXAMPLE 8

Sertraline mandelate (10 gm) is suspended in tert-amyl alcohol (65 ml) at 25-30° C., pH of the mass is adjusted to 2.0 with conc. hydrochloric acid (36%) at 25-30° C. and then stirred for 8 hours at 25-30° C. Filtered the solid and dried at 60° C. for 3 hours 30 minutes to give 4.3 gm of sertraline hydrochloride crystalline form II.

We claim:

1. A process for preparation of sertraline hydrochloride crystalline form II which comprises:

a) adding sertraline free base or sertraline mandelate to a solvent selected from isoamyl alcohol, tert-amyl alcohol and an ester formed by isoamyl alcohol and $C_1$-$C_3$-carboxylic acid;

b) adding hydrochloric acid; and c) isolating sertraline hydrochloride crystalline form II.

2. The process as claimed in claim 1, wherein sertraline free base is dissolved in the solvent before the addition of hydrochloric acid.

3. The process as claimed in claim 1, wherein the solvents to which sertraline free base or sertraline mandelate added are isoamyl alcohol, tert-amyl alcohol, isoamyl formate and isoamyl acetate.

4. The process as claimed in claim 3, wherein the solvent is selected from isoamyl alcohol and tert-amyl alcohol.

5. The process as claimed in claim 4, wherein the solvent is isoamyl alcohol.

6. The process as claimed in claim 1, wherein hydrochloric acid is added in any form that is as an aqueous hydrochloric acid, hydrogen chloride gas or hydrogen chloride in an organic solvent such as methanol, ethanol, isopropyl alcohol, isoamyl alcohol, acetone and ethyl acetate.

7. The process as claimed in claim 1, wherein sertraline mandelate is dissolved or suspended in the organic solvent before the addition of hydrochloric acid.

8. The process as claimed in claim 1, wherein the isolation of sertraline hydrochloride crystalline form II is initiated by a method such as cooling, seeding, partial removal of the solvent from the solution, addition of precipitating solvent or a combination thereof.

9. The process as claimed in claim 8, wherein the isolation is carried out by cooling to obtain sertraline hydrochloride crystalline form II.

10. The process as claimed in claim 1, wherein the addition of hydrochloride to the solution of sertraline free base and isolation of sertraline hydrochloride crystalline form II are carried out at about 0° C. to boiling temperature of the solvent used.

11. The process as claimed in claim 10, wherein the addition of hydrochloric acid is carried out at about 0° C. to 60° C.

12. The process as claimed in claim 11, wherein the addition of hydrochloric acid is carried out at about 0° C. to 40° C.

13. The process as claimed in claim 12, wherein the addition of hydrochloric acid is carried out at about 0° C. to 30° C.

* * * * *